(12) United States Patent
Mir et al.

(10) Patent No.: US 12,410,127 B1
(45) Date of Patent: Sep. 9, 2025

(54) GREEN SYNTHESIS METHOD FOR FORMING SUBSTITUTED PYRROLES

(71) Applicant: PRINCE MOHAMMAD BIN FAHD UNIVERSITY, Dhahran (SA)

(72) Inventors: M. Amin Mir, Dhahran (SA); Syed M. Hasnain, Dhahran (SA); K. Andrews, Dhahran (SA)

(73) Assignee: PRINCE MOHAMMAD BIN FAHD UNIVERSITY, Dhahran (SA)

( * ) Notice: Subject to any disclaimer, the term of this patent is extended or adjusted under 35 U.S.C. 154(b) by 0 days.

(21) Appl. No.: 19/187,833

(22) Filed: Apr. 23, 2025

(51) Int. Cl.
*C07D 207/323* (2006.01)
*C07D 207/333* (2006.01)

(52) U.S. Cl.
CPC ..... *C07D 207/323* (2013.01); *C07D 207/333* (2013.01)

(58) Field of Classification Search
CPC ................................................ C07D 207/323
See application file for complete search history.

(56) References Cited

FOREIGN PATENT DOCUMENTS

| CN | 109632921 B | 2/2021 |
| EP | 0 002 392 A2 | 6/1979 |
| WO | 2024/134488 A1 | 6/2024 |

OTHER PUBLICATIONS

Anis Ahmed Sheikh, et al., "Lemon Juice Catalyzed Synthesis of N-Substituted Pyrrole by Paal-Knorr Reaction", International Journal of Scientific Research in Science, Engineering and Technology, vol. 4, Issue 10, Sep.-Oct. 2018, pp. 176-180, 6 pages.
Farzaneh Mohamadpour, "Malonic Acid as A Green and Efficient Catalyst for the Mass-Scale Synthesis of Pyrrole Medicinal Drugs", Makara Journal of Science, vol. 24, Issue 3, Sep. 18, 2020, pp. 188-193, 7 pages.
Anis Ahmed Sheikh, et al., "Efficient and Environmentally Benign Synthesis of Quinoxaline Catalysed by Fruit Juice", International Journal of Scientific Research in Chemistry (IJSRCH), vol. 5, Issue 1, Jan.-Feb. 2020, pp. 1-5.
U.S. Appl. No. 19/187,847, filed Apr. 23, 2025, Mir, et al.
U.S. Appl. No. 19/187,874, filed Apr. 23, 2025, Mir, et al.
U.S. Appl. No. 19/187,339, filed Apr. 23, 2025, Mir, et al.

*Primary Examiner* — Kamal A Saeed
(74) *Attorney, Agent, or Firm* — Oblon, McClelland, Maier & Neustadt, L.L.P.

(57) ABSTRACT

A green synthetic method for making a pyrrole. The method includes reacting an aryl amine with a compound having a furan moiety in the presence of an organic catalyst that contains juice.

14 Claims, 8 Drawing Sheets

GREEN SYNTHESIS METHOD FOR FORMING SUBSTITUTED PYRROLES

BACKGROUND

Technical Field

The present disclosure is directed towards a green synthesis method for making a pyrrole, and more particularly, the use of a green catalyst for effecting reaction between an amine and a furan-based compound.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Pyrroles are an important class of heterocyclic compounds with widespread applications in medicinal chemistry, materials science, and agrochemicals. They serve as key structural motifs in natural products such as porphyrins, chlorophyll, heme, and vitamin B 12. Additionally, pyrrole derivatives are integral components of many bioactive molecules, including pharmaceuticals with antibacterial, antiviral, anti-inflammatory, and anticancer properties. Examples of pyrroles as pharmaceuticals include Ketorolac, Sunitinib, A torvastatin and Remdisivir. Given their diverse biological and industrial significance, the development of efficient methods for pyrrole synthesis has been a major area of interest in organic chemistry.

Several methods exist for pyrrole synthesis, with the Paal-Knorr reaction being one of the most widely used. This reaction involves the cyclization of a 1,4-dicarbonyl compound with a primary amine under acidic conditions, producing a substituted pyrrole. Other conventional approaches include the Hantzsch pyrrole synthesis, the Knorr synthesis, and the Van Leusen pyrrole synthesis. While these methods have been extensively employed, they present several challenges and limitations.

One major drawback of traditional pyrrole synthesis is the reliance on hazardous reagents and harsh reaction conditions. Many protocols involve the use of strong acids, toxic metal catalysts, or organic solvents such as toluene, benzene, and dichloromethane, which pose environmental and health risks. Additionally, metal-based catalysts, including titanium and bismuth compounds, contribute to high costs and generate toxic waste, complicating purification and disposal. Further, these reactions may require high temperatures or are incompatible with certain functional groups, limiting the scope of pyrroles that can be prepared using these methods. This need for stringent reaction conditions, prolonged reaction times, and low atom economy further hinders the sustainability of these processes.

As green chemistry principles gain prominence, there is a growing demand for environmentally friendly and sustainable alternatives for pyrrole synthesis. Efforts to minimize the use of hazardous chemicals, replace toxic solvents with water-based systems, and develop recyclable catalysts have been actively pursued. However, it is often difficult to achieve acceptable reaction outcomes, such as good yields, high efficiency, scalability, and cost-effectiveness for these methods. Consequently, there is a need for novel methodologies that provide a cleaner, safer, and more sustainable route for pyrrole synthesis without compromising yield or functional group compatibility.

Accordingly, it is one object of the present disclosure to provide methods and systems that may circumvent the drawbacks, such as complexity, high cost, lack of multiphase integration and precision, of the materials known in the art.

SUMMARY

According to a first aspect, the present disclosure relates to a method of forming a pyrrole by reacting an amine and a furan-based compound in the presence of a green catalyst.

In another embodiment the green catalyst is a juice from a fruit.

In some embodiments, the amine may have formula (2)

In some embodiments the furan-based compound may have formula (3)

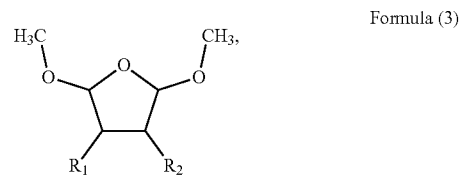

where $R_1$ and $R_2$ are each independently a hydrogen, an optionally substituted alkyl, an optionally substituted cycloalkyl, an optionally substituted arylalkyl, or an optionally substituted aryl; and $R_3$ is a hydrogen, an optionally substituted alkyl, an optionally substituted cycloalkyl, an optionally substituted arylalkyl, or an optionally substituted aryl.

In some embodiments, the catalyst includes a juice from a fruit of a plant in the genus *Malus* and is present in an amount to provide an amount or organic acid present in the juice of 1 to 25 mol % based on a number of moles of amine present.

In some embodiments, the catalyst including juice from a fruit of a plant in the genus *Malus* includes greater than 70 mol % malic acid based on a total number of moles of organic acids present in the juice from a fruit of a plant in the genus *Malus*.

In some embodiments, the catalyst including juice from a fruit of a plant in the genus *Malus* includes malic acid and at least one organic acid selected from the group consisting of quinic acid, shikimic acid, and citric acid.

In some embodiments, the catalyst including juice from a fruit of a plant in the genus *Malus* includes malic acid and citric acid and has a ratio of an amount of malic acid to an amount of citric acid of 20:1 to 50:1.

In some embodiments, the juice from a fruit of a plant in the genus *Malus* includes 0.25 to 2.5 wt %. organic acid, based on a total weight of the juice from a fruit of a plant in the genus *Malus* comprises.

In some embodiments, the method of reacting the amine of formula (2) with the compound of formula (3) is performed substantially free of an organic solvent.

In some embodiments, the compound of formula (3) is 2,5-dimethoxytetrahydrofuran.

In some embodiments, a yield of the compound of formula (1) of greater than 50% based on a total number of moles of amine of formula (2).

The present disclosure also relates to a method of forming a N-substituted pyrrole of formula (4). In some embodiments, the method includes reacting an amine of formula (5) with a compound of formula (6) in the presence of a catalyst including juice from a fruit of a plant in the genus *Malus*,

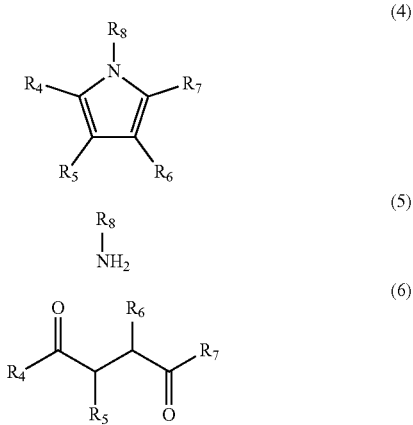

where $R_4$, $R_5$, $R_6$, and $R_7$ are each independently a hydrogen, an optionally substituted alkyl, an optionally substituted cycloalkyl, an optionally substituted arylalkyl, or an optionally substituted aryl; or wherein any two of $R_4$, $R_5$, $R_6$, and $R_7$ together form a five-, six-, or seven-membered ring with the carbon atoms to which they are attached; and $R_8$ is a hydrogen, an optionally substituted alkyl, an optionally substituted cycloalkyl, an optionally substituted arylalkyl, or an optionally substituted aryl.

In some embodiments, the method of reacting the amine of formula (5) with the compound of formula (6) is performed at 25 to 75° C.

In some embodiments, the catalyst including juice from a fruit of a plant in the genus *Malus* is present in an amount to provide an amount or organic acid present in the juice of 1 to 25 mol % based on a number of moles of amine present.

In some embodiments, the catalyst including juice from a fruit of a plant in the genus *Malus* includes greater than 70 mol % malic acid based on a total number of moles of organic acids present in the juice from a fruit of a plant in the genus *Malus*.

In some embodiments, the catalyst including juice from a fruit of a plant in the genus *Malus* includes malic acid and at least one organic acid selected from the group consisting of quinic acid, shikimic acid, and citric acid.

In some embodiments, the catalyst including juice from a fruit of a plant in the genus *Malus* includes malic acid and citric acid and has a ratio of an amount of malic acid to an amount of citric acid of 20:1 to 50:1.

In some embodiments, the juice from a fruit of a plant in the genus *Malus* includes 0.25 to 2.5 wt %. organic acid, based on a total weight of the juice from a fruit of a plant in the genus *Malus* comprises.

In some embodiments, the method of reacting the amine of formula (5) with the compound of formula (6) is performed substantially free of an organic solvent.

In some embodiments, the compound of formula (2) is 2,5-hexanedione.

In some embodiments, a yield of the compound of formula (1) of greater than 50% based on a total number of moles of amine of formula (2).

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
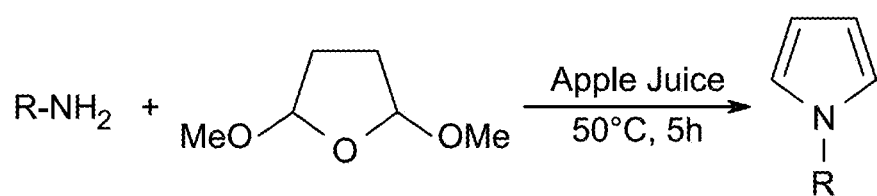
FIG. 1 is a schematic diagram of a reaction of an amine with dimethoxytetrahydrofuran, according to certain embodiments.

When describing the present disclosure, the terms used are to be construed in accordance with the following definitions, unless a context dictates otherwise.

Embodiments of the present invention will now be described more fully hereinafter with reference to the accompanying drawings wherever applicable, in that some, but not all, embodiments of the disclosure are shown.

In the drawings, like reference numerals designate identical or corresponding parts throughout the several views. Further, as used herein, the words 'a,' 'an' and the like generally carry a meaning of 'one or more,' unless stated otherwise.

Furthermore, the terms 'approximately,' 'approximate,' 'about,' and similar terms generally refer to ranges that include the identified value within a margin of 20%, 10%, or preferably 5%, and any values therebetween.

As used herein, the term 'room temperature' refers to a temperature range of '25 degrees Celsius (° C.)±3° C.

As used herein, the term 'catalyst' refers to a substance that facilitates or accelerates a chemical reaction without being consumed in the process, including but not limited to natural catalysts such as fruit juices, which provide inherent acidity and bioactive compounds to promote sustainable and green synthesis.

As used herein, the term 'N-substituted pyrrole' refers to a pyrrole compound in which the nitrogen atom is bonded to a substituent group, such as an alkyl, aryl, acyl, or other functional group, modifying its chemical and physical properties, which may be useful for various applications such as material sciences, agrochemicals, and pharmaceuticals.

As used herein, the genus *Malus* refers to a genus of flowering plants in the Rosaceae family, commonly known as apple trees, which produce fruits rich in organic acids and bioactive compounds.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100%.

The present disclosure is intended to include all hydration states of a given compound or formula, unless otherwise noted or when heating a material.

In addition, the present disclosure is intended to include all isotopes of atoms occurring in the present compounds and complexes. Isotopes include those atoms having the same atomic number but different mass numbers. By way of general example, and without limitation, isotopes of hydrogen include deuterium and tritium, and isotopes of carbon include $^{13}C$ and $^{14}C$. Isotopes of oxygen include $^{16}O$, $^{17}O$, and $^{18}O$. Isotopically-labeled compounds of the disclosure may generally be prepared by conventional techniques known to those skilled in the art or by processes analogous to those described herein, using an appropriate isotopically-labeled reagent in place of the non-labeled reagent otherwise employed.

The term "alkyl," by itself or as part of another substituent, means, unless otherwise stated, a straight (i.e., unbranched) or branched carbon chain (or carbon), or a combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs, and isomers of, for example, n-pentyl, n-hexyl, n-heptyl, n-octyl, and the like. An unsaturated alkyl group has one or more double or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the term "cyclic hydrocarbon" or "cycloalkyl" refers to a cyclized alkyl group. Exemplary cyclic hydrocarbon (i.e., cycloalkyl) groups include but are not limited to, cyclopropyl, cyclobutyl, cyclopentyl, cyclohexyl, norbornyl, and adamantyl. Branched cycloalkyl groups, such as exemplary 1-methylcyclopropyl and 2-methylcyclopropyl groups, are included in the definition of cycloalkyl used in the present disclosure.

As used herein, the term "substituted" refers to at least one hydrogen atom that is replaced with a non-hydrogen group, provided that normal valencies are maintained and that the substitution results in a stable compound. When a compound or a R group (denoted as $R_1$, $R_2$, and so forth) is noted as "optionally substituted", the substituents are selected from the exemplary group including, but not limited to, aroyl (as defined hereinafter), halogen (e.g. chlorine, bromine, fluorine or iodine), alkoxy (i.e. straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy), cycloalkyloxy including cyclopentyloxy, cyclohexyloxy, and cycloheptyloxy, aryloxy including phenoxy and phenoxy substituted with halo, alkyl, alkoxy, and haloalkyl (which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3,3-trifluoropropyl, 1,1,2,2-tetrafluoroethyl, 2,2,3,3-tetrafluoropropyl), hydrocarbyl, arylalkyl, hydroxy, alkoxy, oxo, alkanoyl, alkanoyloxy, amino, alkylamino, arylamino, arylalkylamino, disubstituted amines (e.g. in which the two amino substituents are selected from the exemplary group including, but not limited to, alkyl, aryl, or arylalkyl), alkanylamino, arylamino, alkanoylamino, thiol, alkylthio, arylthio, arylalkylthio, alkylthiono, arylthiono, aryalkylthiono, alkylsulfonyl, arylsulfonyl, arylalkylsulfonyl, sulfonamido (e.g. —$SO_2NH_2$), substituted sulfonamide, nitro, cyano, carboxy, carbamyl (e.g. —$CONH_2$, —CONHalkyl, —CONHaryl, —CONHarylalkyl or cases where there are two substituents on one nitrogen from alkyl, aryl, or arylalkyl), alkoxycarbonyl, aryl, guanidine, heteroarylcarbonyl, heterocyclyl, and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

As used herein, the term "arylalkyl" as used in this disclosure refers to a straight or branched chain alkyl moiety having 1 to 8 carbon atoms that are substituted by an aryl group or a substituted aryl group having 6 to 12 carbon atoms and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl) propyl.

As used herein, the term 'optionally substituted alkyl' refers to an alkyl group which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl) optionally substituted with one or two groups independently selected from alkyl, hydroxyl, alkoxy, alkylsulfonyl, halo, or —CONRR' where R and R' are as defined above.

As used herein, the term 'optionally substituted cycloalkyl' refers to a cycloalkyl group which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl) or heterocyclic (preferably heterocycloamino) optionally substituted with one or two groups independently selected from alkyl, hydroxyl, alkoxy, alkylsulfonyl, halo, or —CONRR' where R and R' are as defined above.

The term 'optionally substituted alkoxy' refers to an alkoxy group which is substituted with one, two, or three substituents independently selected from hydroxyl, alkoxy, carboxy, cyano, alkoxycarbonyl, alkylthio, alkylsulfonyl, halo, haloalkoxy, —CONRR' or —NRR' (where each R is hydrogen, alkyl, hydroxyalkyl, or alkoxyalkyl, and each R' is hydrogen, alkyl, or cycloalkyl) or (preferably heterocycloamino) optionally substituted with one or two groups independently selected from alkyl, hydroxyl, alkoxy, alkylsulfonyl, halo, or —CONRR' where R and R' are as defined above.

As used herein, the term 'optionally substituted arylalkyl group' refers to a structural moiety in organic chemistry that combines an aryl group with an alkyl group, with the option for one or more hydrogen atoms within either or both groups to be replaced by other substituents. The aryl group is a hydrocarbon ring structure derived from benzene, characterized by its alternating single and double bonds. The alkyl group is a hydrocarbon chain structure composed of carbon and hydrogen atoms. When the term 'optionally substituted' is used, it indicates that certain hydrogen atoms within the aryl or alkyl portion of the molecule can be replaced by other functional groups or atoms.

As used herein, the term 'optionally substituted aryl group' refers to a chemical structure consisting of a ring of carbon atoms, typically derived from benzene, with the option for one or more hydrogen atoms on the ring to be replaced by other substituents. Aryl groups are characterized by a delocalized x-electron system resulting from alternating single and double bonds within the ring. The term 'optionally substituted' indicates that the aryl ring may have additional functional groups attached to it.

As used herein, the term 'hydroxyl group' refers to the functional group with the chemical formula —OH and composed of one oxygen atom covalently bonded to one hydrogen atom.

As used herein, the term 'halogen group' refers to the group in the periodic table consisting of six chemically related elements: fluorine (F), chlorine (CI), bromine (Br), or iodine (I).

As used herein, the term 'amine group' refers to the compound and functional group that contains a basic nitrogen atom with a lone pair. Amines are formally derivatives of ammonia, where one or more hydrogen atoms have been replaced by a substituent such as an alkyl or aryl group. A mine may be a primary amine, secondary or a tertiary amine.

As used herein, the term 'nitro group' refers to the functional group consisting of a nitrogen atom bonded to two oxygen atoms (—$NO_2$). The nitro group is typically electron-withdrawing, influencing the reactivity of the compound.

As used herein, the term 'cyano group' refers to the functional group consisting of a carbon atom triple-bonded to a nitrogen atom (—CN).

The present disclosure relates to an environmentally friendly process for synthesizing N-substituted pyrroles using apple juice as a sustainable catalyst. This process enables the cyclization of primary amines with dimethoxy tetrahydrofuran or 2,5-hexanedione under mild conditions without hazardous chemicals.

According to a first aspect, the present disclosure relates to a method of forming an N-substituted pyrrole of formula (1). In some embodiments, the method includes reacting an amine of formula (2) with a compound of formula (3) in the presence of a catalyst. FIG. 1 illustrates the reaction between amine and dimethoxy tetrahydrofuran, which forms the basis of the pyrrole synthesis. The chemical structures of compounds of formula (1), (2), and (3) are depicted below.

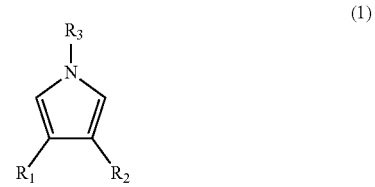

(1)

(2)

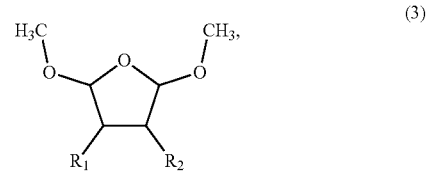

(3)

where $R_1$ and $R_2$ are each independently a hydrogen, an optionally substituted alkyl, an optionally substituted cycloalkyl, an optionally substituted arylalkyl, or an optionally substituted aryl or $R_1$ and $R_2$ together form a five-, six-, or seven-membered ring with the carbon atoms to which they are attached. $R_3$ is a hydrogen, an optionally substituted alkyl, an optionally substituted cycloalkyl, an optionally substituted arylalkyl, or an optionally substituted aryl.

In general, the amine of formula (2) can be any suitable primary amine known to one of ordinary skill in the art. In some embodiments, the amine of formula (2) is an arylamine. An arylamine is amine in which $R_3$ is an aryl group.

In some embodiments, the compound of formula (3) is 2,5-dimethoxytetrahydrofuran. 2,5-dimethoxytetrahydrofuran corresponds to a compound of formula (3) in which $R_1$ and $R_2$ are each hydrogen.

In some embodiments, the compound of formula (3) is a compound of formula (7)

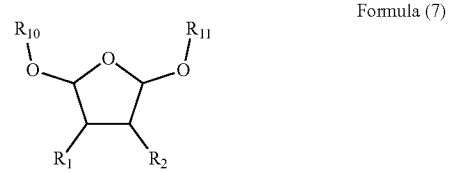

Formula (7)

where $R_1$ and $R_2$ are each independently a hydrogen, an optionally substituted alkyl, an optionally substituted cycloalkyl, an optionally substituted arylalkyl, or an optionally substituted aryl or $R_1$ and $R_2$ together form a five-, six-, or seven-membered ring with the carbon atoms to which they are attached, and where $R_{10}$ and $R_{11}$ are each independently a an optionally substituted alkyl, an optionally substituted cycloalkyl, an optionally substituted arylalkyl. In some embodiments, $R_{10}$ and $R_{11}$ can each independently be methyl, ethyl, n-propyl, isopropyl, n-butyl, sec-butyl, tert-butyl, benzyl, cyclohexyl, or cyclopentyl.

In some embodiments, the catalyst includes juice from a fruit of a plant in the genus *Malus*. In general, the juice can be obtained from any suitable fruit of any suitable plant in the genus *Malus*. Examples of species belonging to genus *Malus* include, but are not limited to, *Malus angustifolia, Malus asiatica, Malus baccata, Malus brevipes, Malus coronaria, Malus crescimannoi, Malus daochengensis, Malus domestica., Malus doumeri, Malus florentina, Malus fusca, Malus halliana, Malus honanensis, Malus hupehensis, Malus ioensis, Malus jinxianensis, Malus kansuensis, Malus komarovii. Malus leiocalyca, Malus mandshurica, Malus muliensis, Malus niedzwetzkyana, Malus ombrophila, Malus orientalis, Malus prattii, Malus prunifolia, Malus rockii, Malus sikkimensis, Malus spectabilis, Malus spontanea, Malus sylvestris, Malus toringo, Malus sargentii, Malus sieboldii, Malus toringoides, Malus transitoria, Malus trilobata, Malus turkmenorum, Malus sieversii, Malus yunnanensis, Malus zhaojiaoensis.*

In some embodiments, the catalyst includes juice from the fruit of *Malus domestica*, the domestic apple (also known as the orchard apple). In general, the domestic apple plant can be any suitable sub-species, cultivar, or variety. Examples of varieties of dometic apples include, but are not limited to Adams Pearmain, Aia Ilu, Airlie Red Flesh, Akane, Åkerö, Alkmene, Allington Pippin, Ambrosia, Anna, Annurca, Antonovka, A pi Etoile, Arctic Apples, Ariane, Arkansas Black, Ashmead's Kernel, Aurora Golden Gala, Autumn Bough, Autumn Glory, Bailey Sweet, Baldwin, Ballyfatten, Beacom, Beauty of Bath, Beauty of Kent, Bellflower apple, Ben Davis, Birgit Bonnier, Bismarck, Black Diamond Apple, Black Gilliflower, Blenheim Orange, Bloody Ploughman, Blue Pearmain, Braeburn, Brina, Brown Snout, Calville Blanc d'hiver, Cameo, Campanino, Cap of Liberty, Cellini, Champion, Chelmsford Wonder, Chisel Jersey, Cider apple, Civni apple, Clarke Pearmain, Claygate Pearmain, Clivia, Coccagee, Cornish Aromatic, Cornish Gilliflower, Cosmic Crisp, Costard, Court Pendu Plat, Cox's Orange Pippin, Creston, Crimson Beauty, Crimson Bramley, Crimson Delight, Crimson Gold, Crimson King, Cripps Pink, Cripps Red, Dabinett, Delbard Jubilée, Delbarestivale, Delrouval, Detroit Red, Devonshire Quarrenden, Discovery, Dorsett Golden, Dougherty, Duchess of Oldenburg, Dufflin, Duke of Devonshire, Dumelow's Seedling, Dutch Mignonne, Edelborsdorfer, Ellis Bitter, Ellison's Orange, Elstar, English Russet, Envy, Eva, EverCrisp, *Malus* 'Evereste', Fiesta, Filippa, Flamenco, Florina, Flower of Kent, Foxwhelp, Fuji, Gala, Gascoyne's Scarlet, Geheimrat Dr. Oldenburg, Ginger Gold, Glockenapfel, Golden Delicious, Golden Noble, Golden Orange, Golden Reinette, Golden Russet, Golden Spire, Golden Sweet, Goldspur, Granny Smith, Gravenstein, Grenadier, Grimes Golden, Hangdown, Harrison Cider Apple, Hawley apple, Hawthornden apple, Hewe's Crab, Hokuto, Honeycrisp, Indo, Ingrid Marie, James Grieve, Jersey Black, Jonadel, Jubilee apple, Julieta, Jupiter, Kalmar Glasäpple, K anzi, Karmijn de Sonnaville, Katy, Keswick Codlin, Kidd's Orange Red, King Byerd, King of the Pippins, Kingston Black, Knobby Russet, Lady Alice, Lady apple, Lady Williams, Landsberger Reinette, Laxton's Superb, Liberty, Liveland Raspberry apple, Lodi, Lord Lambourne, Lost Apple Project, Lucombe's Seedling, Macoun apple, Maiden Blush apple, Major, Malinda, M alling series, *Malus* 'Hopa', Manks Codlin, Margil, McIntosh, Melba, Melon, Michelin, MN 55, Mutsu, Newton Wonder, Newtown Pippin, Nicola, Nonpareil, Norfolk Biffin, Opal, Ortley, Pam's Delight, Papirovka, Paula Red, Pearmain, Peasgood's Nonsuch, Pink Pearl, Pinova, Poveshon, Rajka, Ralls Janet, Rambo apple, Red Astrachan, Red Delicious, Red Pineapple, Redlove apples, Redstreak, Reinette du Canada, Reinette Simirenko, Rhode Island Greening, Ribston Pippin, Rome apple, Roxbury Russet, Sandow, Sansa apple, Sciros, Sekai Ichi, Slack-ma-Girdle, Sops of Wine, Spartan, and Splendour.

In some embodiments, the juice from a fruit of a plant in the genus *Malus* includes malic acid and at least one organic acid selected from the group including of quinic acid, shikimic acid, and citric acid. In some embodiments, the catalyst may include other organic acids such as acetic acid, ascorbic acid, benzoic acid, butyric acid, caffeic acid, caproic acid, caprylic acid, chlorogenic acid, cinnamic acid, ferulic acid, formic acid, fumaric acid, gallic acid, gluconic acid, glutaric acid, glycolic acid, heptanoic acid, hexanoic acid, isocitric acid, isovaleric acid, lactic acid, maleic acid, mandelic acid, oxalic acid, palmitic acid, phytic acid, propionic acid, salicylic acid, succinic acid, and tartaric acid. In some embodiments, the juice from a fruit of a plant in the genus *Malus* includes malic acid, quinic acid, shikimic acid and citric acid.

In some embodiments, the juice from a fruit of a plant in the genus *Malus* includes malic acid and citric acid and has a ratio of malic acid to citric acid in the range of 20:1 to 50:1 by weight. For example, the juice may have a ratio of malic acid to citric acid of 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, or 50:1.

In some embodiments, the juice from a fruit of a plant in the genus *Malus* includes 0.25 to 2.5 wt. % organic acids, based on total weight of the juice from a fruit of a plant in the genus *Malus*. For example, the juice may contain 0.25 wt. %, 0.30 wt. %, 0.35 wt. %, 0.40 wt. %, 0.45 wt. %, 0.50 wt. %, 0.55 wt. %, 0.60 wt. %, 0.65 wt. %, 0.70 wt. %, 0.75 wt. %, 0.80 wt. %, 0.85 wt. %, 0.90 wt. %, 0.95 wt. %, 1.00 wt. %, 1.05 wt. %, 1.10 wt. %, 1.15 wt. %, 1.20 wt. %, 1.25 wt. %, 1.30 wt. %, 1.35 wt. %, 1.40 wt. %, 1.45 wt. %, 1.50 wt. %, 1.55 wt. %, 1.60 wt. %, 1.65 wt. %, 1.70 wt. %, 1.75 wt. %, 1.80 wt. %, 1.85 wt. %, 1.90 wt. %, 1.95 wt. %, 2.00 wt. %, 2.05 wt. %, 2.10 wt. %, 2.15 wt. %, 2.20 wt. %, 2.25 wt. %, 2.30 wt. %, 2.35 wt. %, 2.40 wt. %, 2.45 wt. %, or 2.50 wt. % based on a total weight of juice.

In some embodiments, the catalyst includes juice from a fruit of a plant in the genus *Malus* includes greater than 70 mol %, preferably greater than 75 mol %, preferably greater than 80 mol %, preferably greater than 85 mol % malic acid based on a total number of moles of organic acids present in the juice from a fruit of a plant in the genus *Malus*.

In some embodiments, the method includes reacting the amine of formula (2) with the compound of formula (3) at 25 to 75° C. For example, the reacting can be performed at 25° C., 30° C., 35° C., 40° C., 45° C., 50° C., 55° C., 60° C., 65° C., 70° C., or 75° C. In some embodiments, the method includes reacting the amine of formula (2) with the compound of formula (3) is performed at 40 to 60° C. Although this step can be performed in the presence of an organic solvent, it is preferred that this step is performed substantially free of an organic solvent. Preferably the reaction is carried out as a mixture consisting of the juice, the amine and the compound containing a furan or hydrofuran moiety. In the context of the present disclosure, the use of a mixture of pure apple juice amine and compound containing a furan or hydrofuran moiety is carried out without added solvent.

In a preferable embodiment, the amine and the furan-based compound, i.e., the compound of formula (3), are first mixed as neat liquids. A juice is then added to the mixture of neat liquids, and the resulting mixture is agitated. Subsequently, a biphasic mixture containing an aqueous phase and an organic phase is added to the reaction mixture. The resulting composition is agitated, for example by shaking, to prepare a reaction composition which is subsequently treated to isolate and identify one or more products. Preferably, the organic catalyst, i.e., the fruit juice, is prepared immediately before its addition to the mixture of the reactants, for example the fruit juice is prepared within 1-24 hours, preferably 2-20 or 4-12 hours before the compounds of formula (1) and (3) are mixed. The utilization of a freshly prepared organic catalyst helps to ensure a reliable mixture of organic acids in the juice.

The biphasic mixture preferably contains an aqueous brine solution and a chlorinated organic solvent such as dichloromethane. The aqueous brine solution contains one or more of sodium chloride, sodium carbonate and sodium bicarbonate. The total amount of by weight of dissolved solids in the brine solution is preferably 2-25 wt. %, 4-28 wt. %, 8-15 wt. % or about 10 wt. % based on the total weight of the brine solution. Preferably sodium chloride is present in a major amount based on the total mass amount of sodium chloride, sodium carbonate and sodium bicarbonate. Preferably the only salts present in the B brinerian solution are sodium chloride, sodium carbonate and sodium bicarbonate.

Examples of organic solvents include, but are not limited to acetonitrile, dimethylformamide (DMF), acetone, N-methyl pyrrolidone (NMP), tetrahydrofuran (THF), hexamethylphosphoramide (HMPA), sulfolane, dimethylacetamide (DMAc), propylene carbonate, γ-butyrolactone, 1,3-dimethyl-2-imidazolidinone (DMI), 1,4-dioxane, ethylene carbonate, methylene chloride, chlorobenzene, toluene, anisole, nitromethane, benzonitrile, dimethyl sulfoxide, 2-methyl-2-pentanone, pyridine, N-ethyl pyrrolidone (NEP), 1-methyl-2-pyrrolidone, methyl ethyl ketone (MEK), dimethoxyethane, trichloromethane, 2,2,2-trifluoroethanolacetone, 1,2-butanediol, 1,3-butanediol, 1,4-butanediol, 2-butoxyethanol, butyric acid, diethanolamine, diethylenetriamine, dimethylformamide, ethanol, ethylamine, ethylene glycol, formic acid, furfuryl alcohol, glycerol, methanol, methyl diethanolamine, methyl isocyanide, 1-propanol, 1,3-propanediol, 1,5-pentanediol, 2-propanol, propanoic acid, propylene glycol, pyridine, tetrahydrofuran, and triethylene glycol.

In some embodiments, the yield of the compound of formula (1) is greater than 50%, preferably greater than 55%, preferably greater than 60%, preferably greater than 65%, preferably greater that 70%, preferably greater that 75%, preferably greater that 80%, preferably greater that 85%, preferably greater than 90%. In some embodiments, the yield of the compound of formula (1) is 91% based on a total number of moles of amine of formula (2).

In some embodiments, the catalyst including juice from a fruit of a plant in the genus *Malus* present in an amount sufficient to provide an amount of organic acid of 1 to 25 mol %, % based on the number of moles of amine present. For example, the catalyst can be present in an amount sufficient to provide an amount of organic acid of 1 mol %, 2.5 mol %, 5 mol %, 7.5 mol %, 10 mol %, 12.5 mol %, 15 mol %, 17.5 mol %, 20 mol %, 22.5 mol %, or 25 mol % based on the number of moles of amine present.

The number of moles of catalyst is preferably calculated based on the total number of moles of malic acid, quinic acid, shikimic acid and citric acid in the juice. The concentrations and amounts of each of malic acid, quinic acid, shikimic acid and citric acid in the juice can be determined by conventional analytical techniques including gas HPLC, mass spectrometry and NMR.

In another embodiment of the present disclosure, the molar amount of catalyst is based on the total titratable acidity in the juice. Total titratable acidity is determined by titrating a solution of 5 ml of the juice in 100 mil distilled water to neutrality (e.g., titrating to the endpoint identified by phenolphthalein indicator) with a standardized sodium hydroxide solution.

The present disclosure also relates to a method of forming an N-substituted pyrrole of formula (4). In some embodiments, the method includes reacting an amine of formula (5) with a compound of formula (6) in the presence of a catalyst. In some embodiments, the catalyst comprises juice from a fruit of a plant in the genus *Malus*. The chemical structures of compounds of formula (4), (5) and (6) are depicted below.

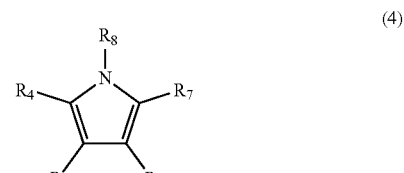

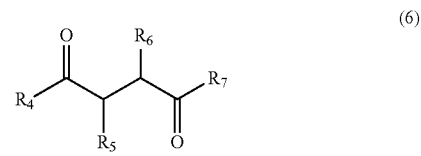

wherein $R_4$, $R_5$, $R_6$, and $R_7$ are each independently a hydrogen, an optionally substituted alkyl, an optionally substituted cycloalkyl, an optionally substituted arylalkyl, or an optionally substituted aryl; or wherein any two of $R_4$, $R_5$, $R_6$, and $R_7$ together form a five-, six-, or seven-membered ring with the carbon atoms to which they are attached; and $R_8$ is a hydrogen, an optionally substituted alkyl, an optionally substituted cycloalkyl, an optionally substituted arylalkyl, or an optionally substituted aryl.

In general, the catalyst can be as described above.

In general, the amine of formula (2) can be any suitable primary amine known to one of ordinary skill in the art. In some embodiments, the amine of formula (2) is an arylamine. An arylamine is amine in which $R_3$ is an aryl group.

In general, the compound of formula (6) can be any suitable 1,4-dicarbonyl known to one of ordinary skill in the art. In some embodiments, the 1,4-dicarbonyl of formula (6) is a 1,4-dione (also known as a 1,4-diketone). A 1,4-dione is a compound of formula (6) in which $R_4$ and $R_7$ are each an optionally substituted alkyl, aryl, cycloalkyl, arylalkyl, or combination of these. This way, the two carbonyl functional groups present between $R_4$ and the carbon attached to $R_5$ and the between $R_7$ and the carbon attached to $R_6$ are ketone functional groups. In some embodiments, the compound of formula (6) is 2,5-hexanedione.

In some embodiments, the method has a yield of the compound of formula (4) of greater than 50%, preferably greater than 55%, preferably greater than 60%, preferably greater than 65%, preferably greater than 70%, preferably greater than 75%, preferably greater than 80%, preferably greater that 85%. In some embodiments, the yield of the compound of formula (4) is 85% based on the total number of moles of the amine of formula (5).

In some embodiment, the method includes reacting the amine of formula (5) with the compound of formula (6) at 25 to 75° C. For example, the reacting can be performed at 25° C., 30° C., 35° C., 40° C., 45° C., 50° C., 55° C., 60° C., 65° C., 70° C., or 75° C. In some embodiments, the method includes reacting the amine of formula (5) with the compound of formula (6) at 40 to 60° C. Although this step can be performed in the presence of an organic solvent, it is preferred that this step be performed substantially free of an organic solvent. In some embodiments, the juice from the fruit of a plan in the genus *Malus* serves as both catalyst and aqueous solvent.

In some embodiment, the catalyst includes juice from a fruit of a plant in the genus *Malus* and is present in an amount sufficient to provide an amount of organic acid of 1 to 25 mol %, % based on the number of moles of amine present. For example, the catalyst can be present in an amount sufficient to provide an amount of organic acid of 1 mol %, 2.5 mol %, 5 mol %, 7.5 mol %, 10 mol %, 12.5 mol %, 15 mol %, 17.5 mol %, 20 mol %, 22.5 mol %, or 25 mol % based on the number of moles of amine present.

The following examples are provided solely for illustration and are not to be construed as limitations of the present disclosure, as many variations thereof are possible without departing from the spirit and scope of the present disclosure.

EXAMPLES

The following examples demonstrate a method of forming a N-substituted pyrrole using apple juice as a sustainable catalyst. The examples are provided solely for illustration and are not to be construed as limitations of the present disclosure, as many variations thereof are possible without departing from the spirit and scope of the present disclosure.

Example 1: Experimental

Purchased chemicals were utilized without additional purification. Using deuterated chloroform (CDC) 3) as the solvent and room-temperature tetramethylsilane (TM S) as the internal standard, 1H and 13C nuclear magnetic resonance (NMR) spectra were analyzed on a 500 megahertz (M Hz) Bruker spectrometer. Coupling constants J are expressed in Hertz (Hz), and chemical shifts are expressed in chemical shift (8) with respect to TM S. For column chromatography, EM silica gel 60 (300-400 mesh) was used.

Example 2: Results

Apple juice (2 mL) was added to amine 1 (1 mmol) along with dimethoxytetrahydrofuran 2 (1 mmol). At 25° C., the reaction mixture was agitated. After adding 10 mL of dichloromethane and 5 mL of brine, the reaction mixture was thoroughly shaken. After being separated, the organic layer was dried using sodium sulfate and then evaporated under low pressure. The reaction mixture was cooled to room temperature, diluted in ethyl acetate, and rinsed with brine after product 3 was purified and seen by TLC and GC-MS analysis. Ethyl acetate was used to extract the $H_2O$ layer once more. To obtain the required product, the mixed organic extracts were dried using $Na_2SO_4$ and concentrated under vacuum. The product 3 that resulted was then refined using silica gel column chromatography (petroleum ether/ethyl acetate).

Table 1

Apple Juice-catalyzed Paal-Knorr reaction of 1 with 2 at 30° C.

| Primary amine | Amount of apple juice | Reaction Time | % Yield |
|---|---|---|---|
| Aniline (1 mmole) | 2 mL | 5 h | 91 |
| 4-methoxy aniline | 2 mL | 6 h | 90 |
| $NH_2(CH_2)_2NH_2$ | 2 mL | 8 h | 84 |
| $PhCH_2NH_2$ | 2 mL | 9 h | 91 |
| 1-naphthylamine | 2 mL | 12 h | 83 |
| 1-aminoanthracene | 2 mL | 15 h | 86 |
| 9-aminophenanthrene | 2 mL | 18 h | 88 |
| 1-aminopyrene | 2 mL | 20 h | 85 |
| aminochrysene | 2 mL | 21 h | 89 |
| 2-aminopyridine | 2 mL | 10 h | 94 |

Figure 2A:
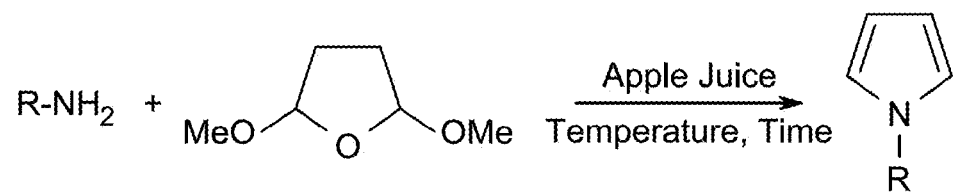
FIG. 2A is a schematic diagram of reactions of an amine and a furan-based compound under certain conditions.

Substances with an electron-donating group reacted more quickly than those with an electron-withdrawing group. Rice malt's acidity activates dimethoxy tetrahydrofuran, which produces dialdehyde in the reaction media. Dehydration and aromatization follow a nucleophilic attack on the carbonyl function to start the process. FIG. 2A focuses on optimizing reaction conditions, specifically temperature and time, to enhance the efficiency of this transformation.

TABLE 2

The effect of temperature and time on the formation of N-substituted pyrroles; [a] Requirements for the reaction include apple juice (10 mol %), 2,5-dimethoxytetrahydrofuran (2 equiv., 2 mmol), and amine (1 equiv., 1 mmol).

| S. N | Temp (° C.) | Time (h) | % Yield, 3a |
|---|---|---|---|
| 1 | RT | 3 | traces |
| 2 | 50 | 3 | 55 |
| 3 | 70 | 4 | 45 |
| 4 | 40 | 3 | 55 |
| 5 | 40 | 5 | 65 |
| 6 | 40 | 7 | 70 |
| 7 | 60 | 7 | 80 |
| 8 | 60 | 9 | 80 |
| 9 | 60 | 10 | 85 |
| 10 | 60 | 20 | 45 |

TABLE 3

Catalyst Concentration effect on the formation of N-substituted pyrroles; reaction conditions: amine (1 equiv., 1 mmol), 2,5-dimethoxytetrahydrofuran (1.5 equiv., 1.5 mmol), apple juice (10 mol %), 50° C., 7 h.

| S. N | Catalyst (y mol %) | Yield, 3a (%) [a] |
|---|---|---|
| 1 | 20 | 85 |
| 2 | 15 | 75 |
| 3 | 10 | 70 |
| 4 | 5 | 70 |
| 5 | 2.5 | 60 |

Figure 2B:
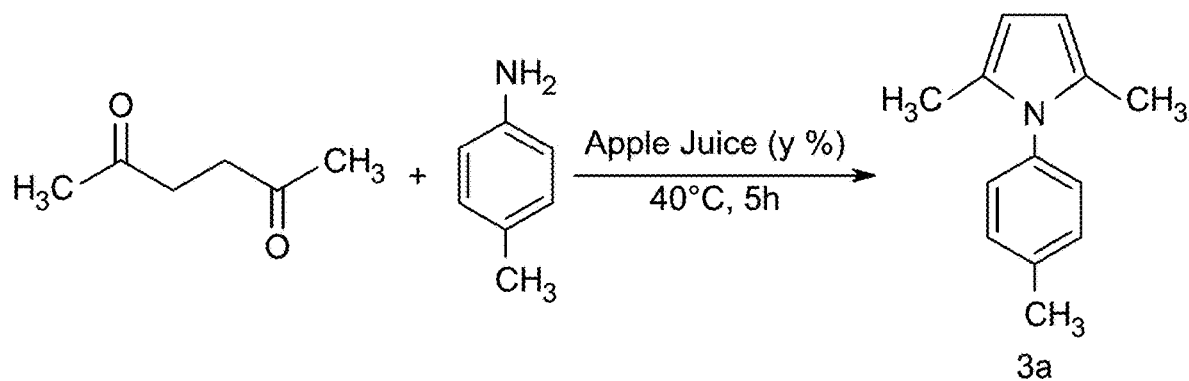
FIG. 2B is a schematic diagram of a reaction of an amine and a furan-based compound under certain conditions to form $C_{13}H_{15}N$ (3a).
Figure 3:
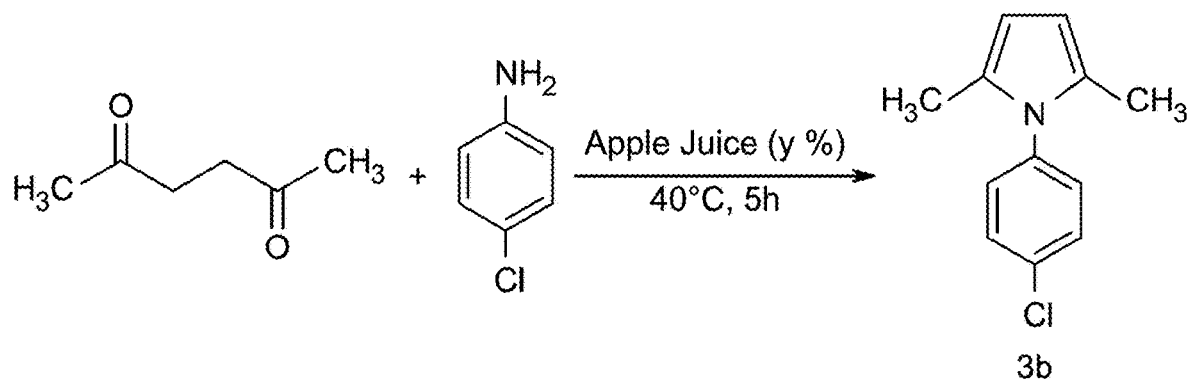
FIG. 3 is a schematic diagram of a reaction of an amine and a furan-based compound under certain conditions to form $C_{12}H_{12}NCl$ (3b).
Figure 4:
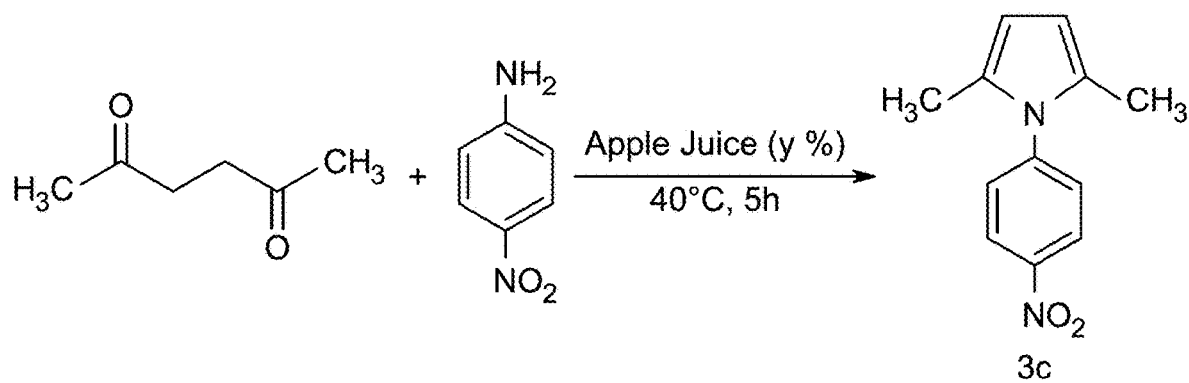
FIG. 4 is a schematic diagram depicting synthesis of $[C_{12}H_{12}NO_2]$ (3c), according to certain embodiments.

An amine (1 mmol), acetonylacetone (1 mmol), and 10 ml of catalyst (apple juice) were heated to 40° C. for five hours without the use of any solvents. Using a combination of n-hexane and ethyl acetate as an eluent, TLC tracked the reaction's development. Ethyl acetate (3 mL) was then used to extract the required chemicals, and centrifugation and filtration were used to separate the catalyst. An n-hexane/ethyl acetate mixture was used as an eluent, and flash column chromatography was used to purify all of the chemicals produced. Using the previously published data and NMR data, these chemicals were identified. FIG. 2B4 details the synthesis of compound $C_{13}H_{15}N$ (3a), while FIG. 3 and FIG. 4 depict the synthesis of $C_{12}H_{12}NCl$ (3b) and $C_{12}H_{12}NO_2$ (3c), respectively, demonstrating variations in functional groups.

Figure 5:
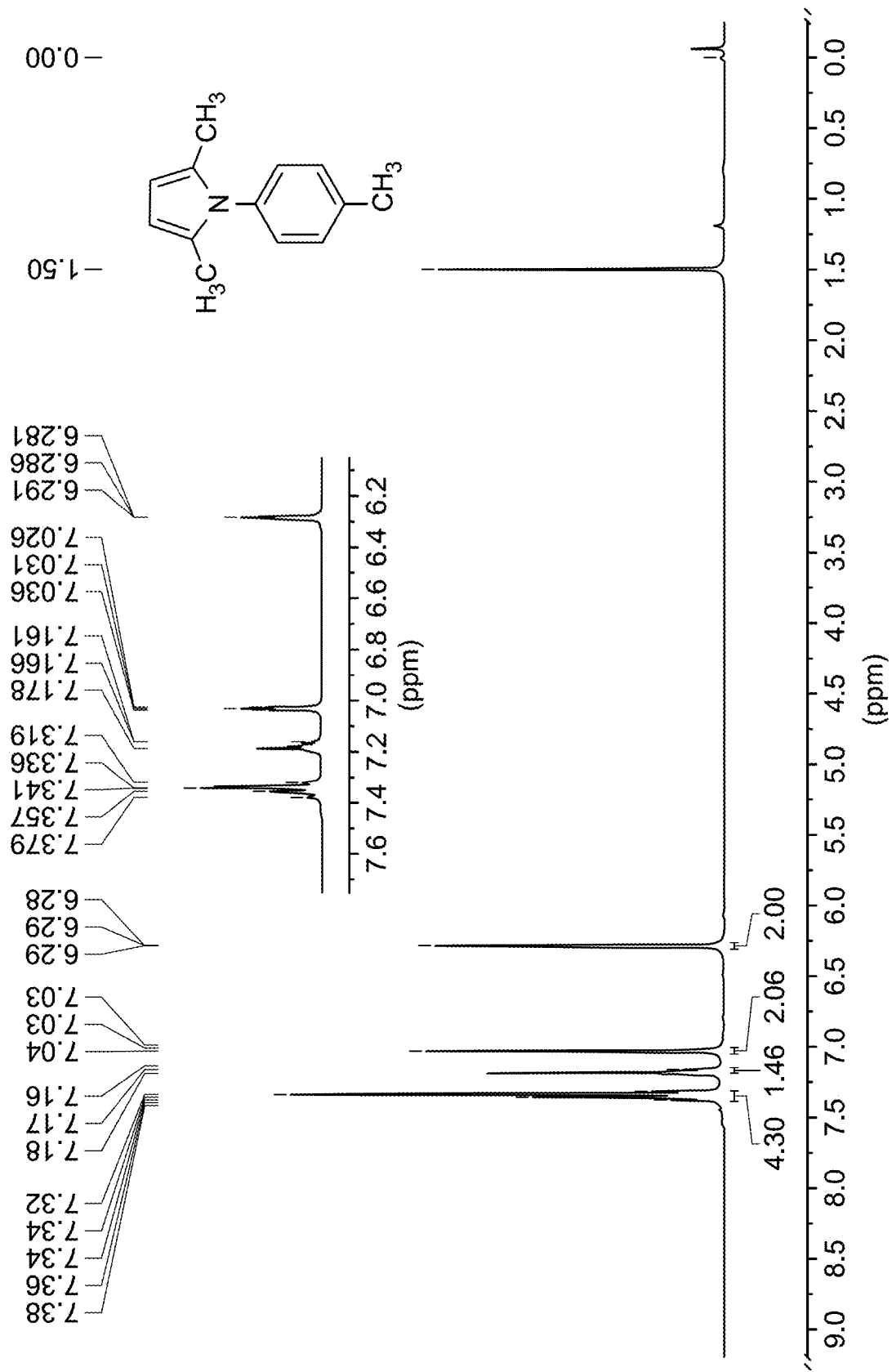
FIG. 5 shows a $^1H$ spectra of compound 3a, according to certain embodiments.
Figure 6:
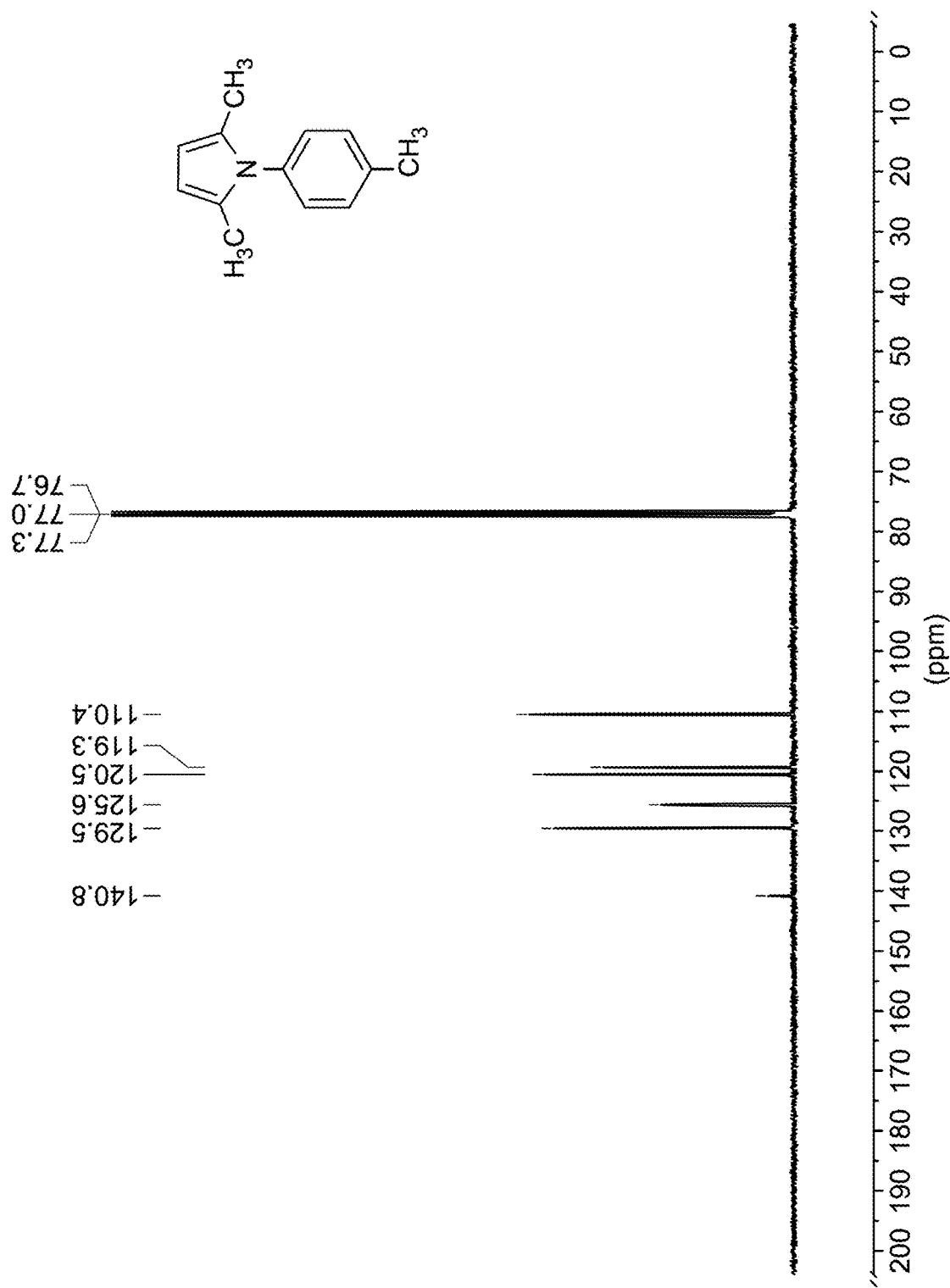
FIG. 6 shows a $^{13}C$ spectra of compound 3a, according to certain embodiments.

Compound 3a was produced as a white solid (130 mg, 65%) by a solvent-free reaction of acetonylacetone 1a (120 μL, 1.5 mmol), 4-methylaniline 2a (80 μL, 1.5 mmol), and 10 ml of catalyst heated to 75° C. for five hours. Rf is 0.21 (100 percent PE). 74-77° C. (lit. 75-78° C.) m.p. δ=3.11 (s, 6H), 2.99 (s, 3H), 4.50 (s, 2H), 6.1 (s, 2H), and 7.10-5.99 (m, 4H) in 1H NMR (495 MHz, $CDCl_3$). FIG. 5 and FIG. 6 show the 1H and 13C NMR spectra of the compound 3a.

Figure 7:
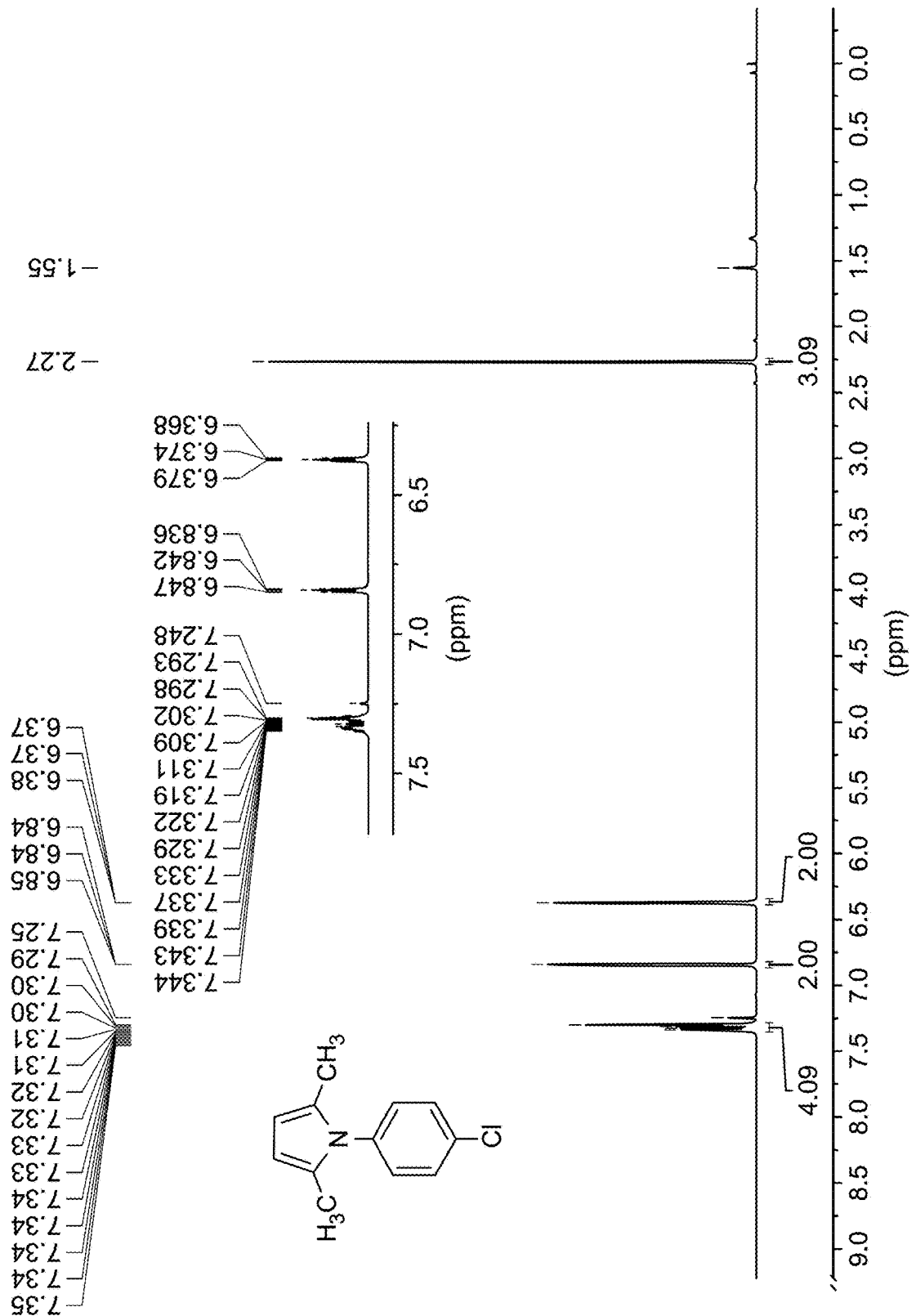
FIG. 7 shows a $^1H$ spectra of compound 3b, according to certain embodiments.
Figure 8:
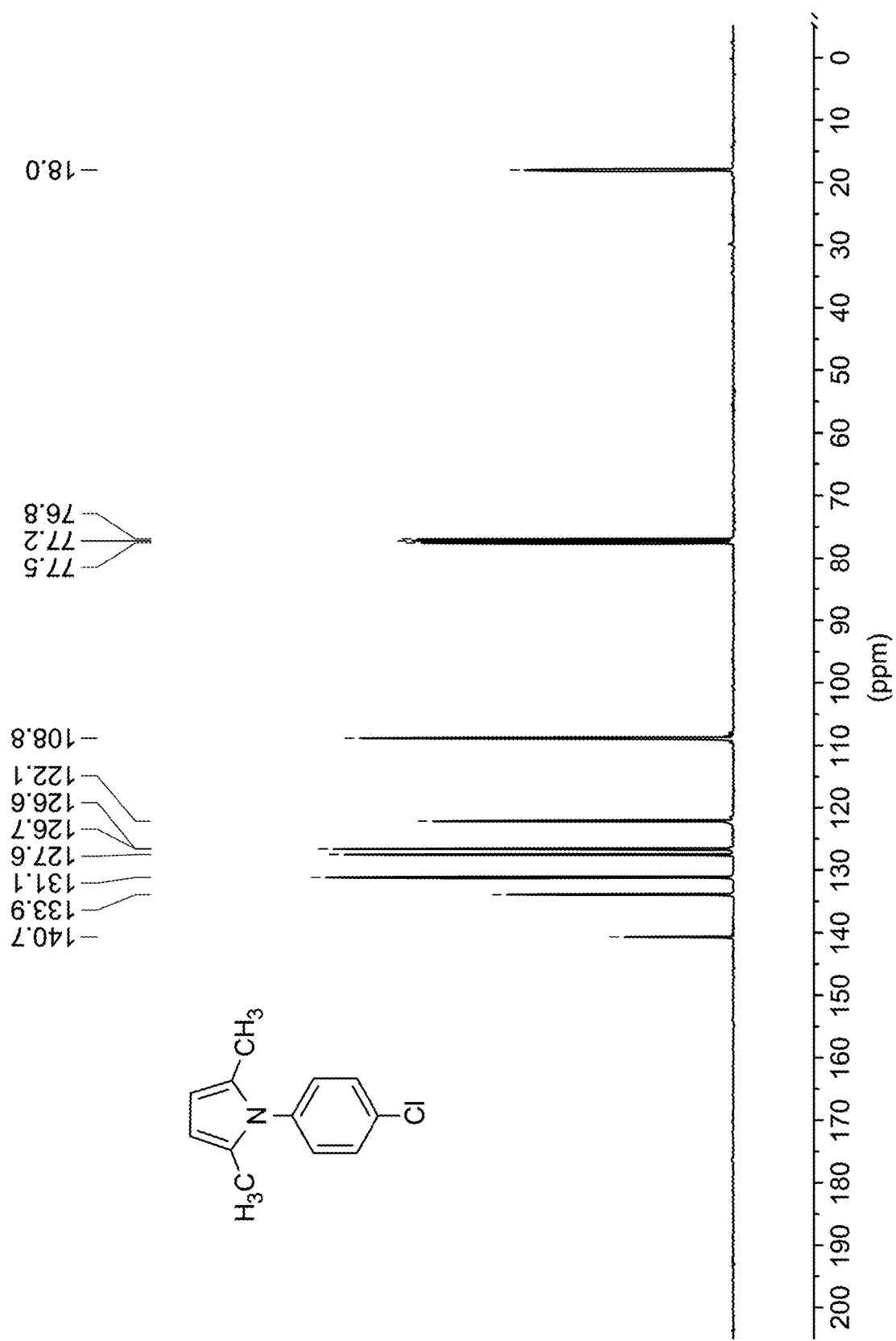
FIG. 8 shows a $^{13}C$ spectra of compound 3b, according to certain embodiments.

A cetonylacetone 1b (120 μL, 1.5 mmol), 4-chloroaniline 2b (130 mg, 1.5 mmol), and 10 ml of catalyst were heated to 75° C. for five hours in a solvent-free reaction. Following silica gel purification with EtOAc/n-hexane (2:31, v/v) as an eluent, compound 3b was obtained as a white solid (181 mg, 779). Rf is 0.51 (100 percent PE). 50-51° C. (lit. 51-520C) m.p. δ=3.11 (s, 6H), 6.11 (s, 2H), 7.20-7.30 (m, 1H), 7.15-7.20 (m, 1H), and 7.50-7.55 (m, 2H) in 1H NMR (495 MHz, $CDCl_3$). FIG. 7 and FIG. 8 correspond to $^1H$ and $^{13}C$ NMR spectra of the compounds 3b.

Figure 9:
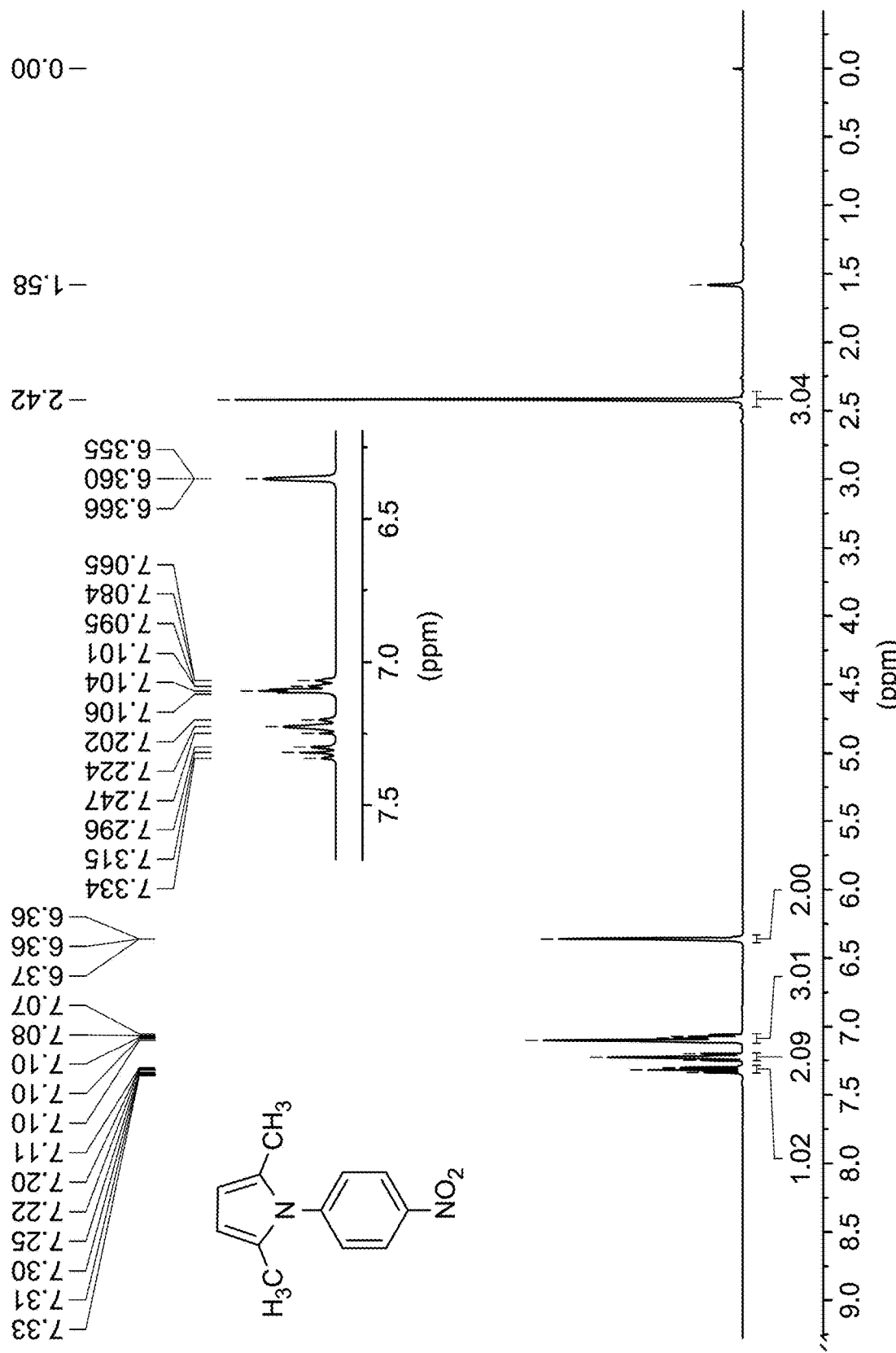
FIG. 9 shows a $^1H$ spectra of compound 3c, according to certain embodiments.
Figure 10:
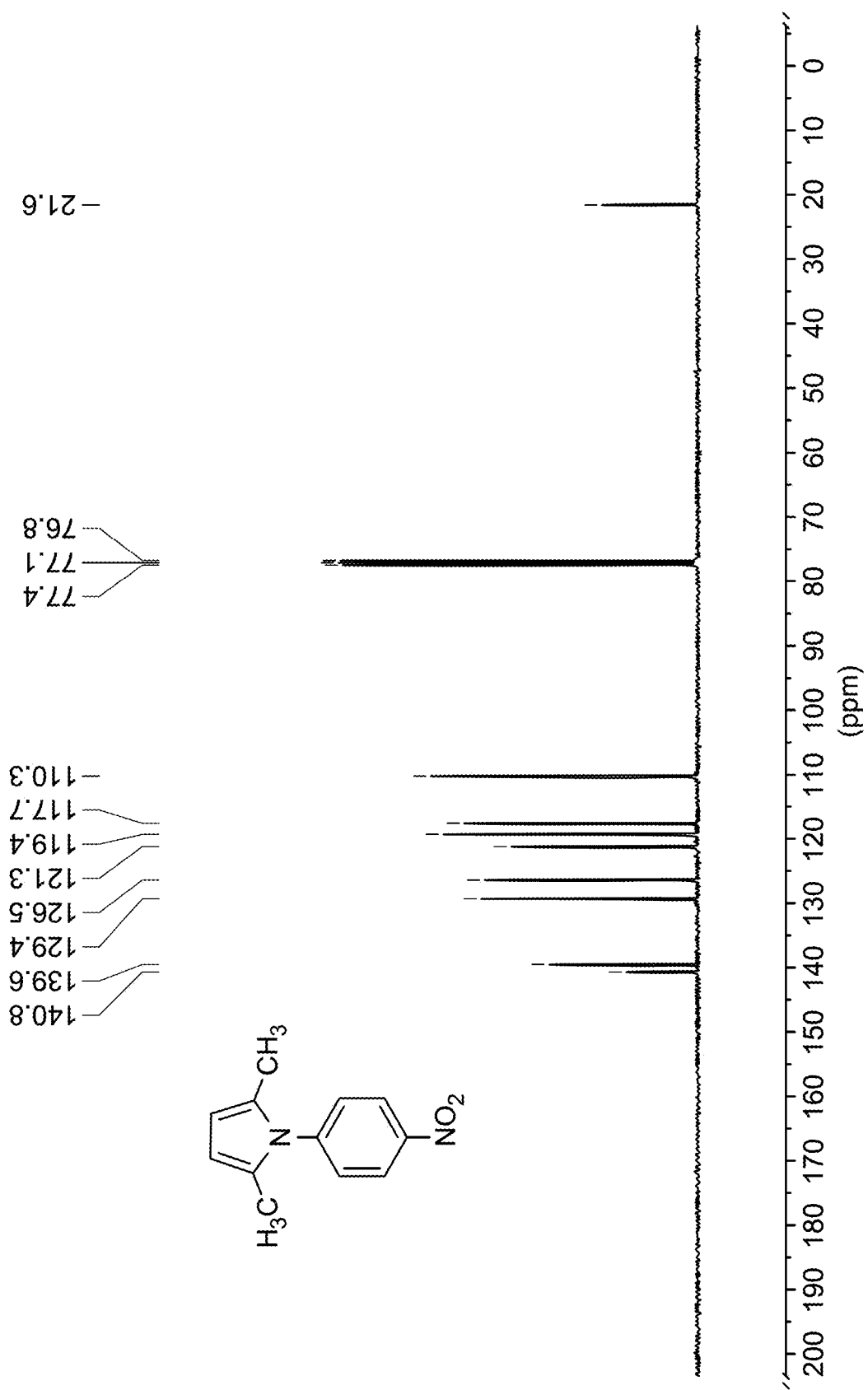
FIG. 10 shows a $^{13}C$ spectra of compound 3c, according to certain embodiments.

A cetonylacetone 1c (120 μL, 1.5 mmol), 4-nitroaniline 2c (125 mg, 1.5 mmol), and 10 ml of catalyst were heated to 75° C. for five hours to conduct a solvent-free reaction to obtain the red solid form of chemical 3c (175 mg, 80%). (PE:EA=9:1) Rf=0.41. (lit. 154-1156° C.) m.p. 152-155° C. δ=1.91 (s, 6H), 6.11 (s, 2H), 6.95-6.99 (m, 2H), and 7.97-7.99 (m, 2H) in 1H NMR (450 M Hz, $CDCl_3$). FIG. 9 and FIG. 10 represent 1H and 13C NMR spectra of the compound 3c.

A sustainable and environmentally friendly method of producing N-substituted pyrroles using the Paal-Knorr reaction is described. Under mild, environmentally benign conditions, the cyclization of primary amines with dimethoxytetrahydrofuran/2, 5-hexanedione was efficiently facilitated by the natural acidity and bioactive chemicals in apple juice, producing pyrrole derivatives. This approach produces high yields and eliminates the necessity for harsh reaction conditions or hazardous reagents. The potential of bio-based materials to promote sustainable organic synthesis is demonstrated by using apple juice as a catalyst. The method offers a cost-effective, sustainable substitute for conventional methods in the production of heterocyclic compounds while also lessening their environmental impact. Given the wide range of uses for pyrrole derivatives in functional materials, agrochemicals, and medicines, this approach has the potential to be scaled up and integrated into commercial applications, opening the door for future synthetic methods that are more environmentally friendly.

Numerous modifications and variations of the present disclosure are possible in light of the above teachings. It is therefore to be understood that within the scope of the appended claims, the invention may be practiced otherwise than as specifically described herein.

The invention claimed is:

1. A green method of forming an N-substituted pyrrole using an organic catalyst, comprising:
    reacting an amine of formula (2) with a compound of formula (3) in the presence of the organic catalyst,

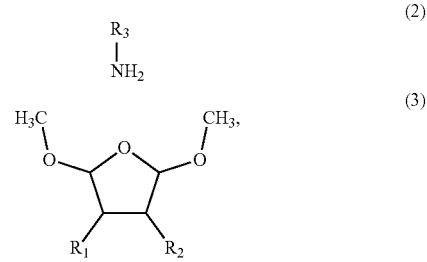

wherein the organic catalyst consists of juice from a fruit of a plant in the genus *Malus*,
wherein the reacting includes mixing in a biphasic medium to form a compound of formula (1)

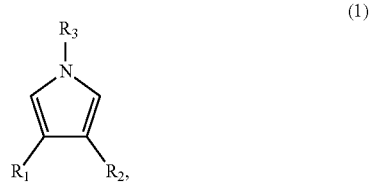

wherein $R_1$ and $R_2$ are each independently a hydrogen, an optionally substituted alkyl, an optionally substituted cycloalkyl, an optionally substituted arylalkyl, or an optionally substituted aryl; and wherein $R_3$ is an optionally substituted aryl.

2. The method of claim 1, wherein the reacting is performed at 25 to 75° C. and the juice is obtained directly from the fruit before the reacting.

3. The method of claim 1, wherein the organic catalyst is present in an amount to provide a total amount of malic acid, quinic acid, shikimic acid, and citric acid of 1 to 25 mol % based on a number of moles of the amine.

4. The method of claim 1, wherein the organic catalyst comprises greater than 70 mol % malic acid based on a total number of moles of organic acids present in the juice.

5. The method of claim 1, wherein the organic catalyst comprises malic acid and at least one organic acid selected from the group consisting of quinic acid, shikimic acid, and citric acid.

6. The method of claim 1, wherein the organic catalyst has a ratio of an amount of malic acid to an amount of citric acid of 20:1 to 50:1.

7. The method of claim 1, wherein the organic catalyst comprises 0.25 to 2.5 wt %. of organic acids, based on a total weight of the juice.

8. The method of claim 1, wherein the reacting is performed substantially free of an organic solvent.

9. The method of claim 1, wherein the compound of formula (2) is 2,5-di methoxytetrahydrofuran.

10. The method of claim 1, wherein the reacting forms the compound of formula (1) in a yield of greater than 50 mol % based on a total number of moles of the amine of formula (2).

11. The method of claim 1, wherein the biphasic medium comprises an aqueous phase and an organic phase.

12. The method of claim 11, wherein the organic phase comprises a chlorinated solvent.

13. The method of claim 12, wherein the aqueous phase is a brine solution comprising at least on of NaCl, $Na_2CO_3$ and $NaHCO_3$.

14. The method of claim 1, further comprising:

macerating the fruit to obtain the juice immediately prior to the reacting, wherein the juice is added to a mixture consisting of the amine and the compound of formula (3) to form a reaction mixture, then the biphasic medium is added to reaction mixture.

* * * * *